United States Patent [19]

DuPriest et al.

[11] Patent Number: 4,659,733
[45] Date of Patent: Apr. 21, 1987

[54] METHOD FOR TREATING HYPERTENSION WITH 2,3-DIAMINO-1,4-BUTANEDITHIOL; 4,5-DIAMINO-1,2-DITHIANE; AND N-ACYL AND N-ALKYL DERIVATIVES THEREOF

[75] Inventors: Mark T. DuPriest, Arlington; Billie M. York, Jr., Fort Worth, both of Tex.

[73] Assignee: Alcon Laboratories, Inc., Fort Worth, Tex.

[21] Appl. No.: 678,833

[22] Filed: Dec. 6, 1984

[51] Int. Cl.$^4$ ............... A61K 31/385; A61K 31/095; A61K 31/13

[52] U.S. Cl. .................................... 514/436; 514/533; 514/538; 514/539; 514/542; 514/550; 514/562; 514/649; 514/650; 514/665; 549/22; 560/8; 560/19; 560/129; 560/147; 560/148; 560/155; 560/158; 562/561; 562/565; 564/164; 564/197; 564/340; 564/500

[58] Field of Search ............... 549/22; 560/8, 19, 129, 560/147, 148, 155, 158; 562/561, 565; 564/164, 197, 340, 500; 514/436, 533, 538, 539, 542, 550, 562, 649, 650, 665

[56] References Cited

U.S. PATENT DOCUMENTS 3,459,198  8/1969  Zemlin et al. .................... 424/71

FOREIGN PATENT DOCUMENTS 0096521  12/1983  European Pat. Off. .............. 424/71
0095916  12/1983  European Pat. Off. .............. 424/71

OTHER PUBLICATIONS

Hever et al, CA, vol. 100 (1984), 100: 85253.

Primary Examiner—Henry R. Jiles
Assistant Examiner—J. G. Mullins
Attorney, Agent, or Firm—James A. Arno; Gregg C. Brown; Robert L. Price

[57] ABSTRACT

Disclosed are 2,3-diamino-1,4-butanedithiol; 4,5-diamino-1,2-dithiane; and their N-acyl and N-alkyl derivatives. Also disclosed are processes for preparing the disclosed compounds; pharmaceutical compositions comprising such compounds; and a method of treatment comprising administering such compounds and compositions when an antihypertensive effect or radioprotective effect is indicated.

7 Claims, No Drawings

METHOD FOR TREATING HYPERTENSION WITH 2,3-DIAMINO-1,4-BUTANEDITHIOL; 4,5-DIAMINO-1,2-DITHIANE; AND N-ACYL AND N-ALKYL DERIVATIVES THEREOF

BACKGROUND OF THE INVENTION

This invention relates to 2,3 diamino-1,4-butanedithiol (I); its dithiane, 4,5-diamino-1,2-dithiane (II); N-acyl, an N-alkyl derivatives thereof; and pharmaceutically acceptable salts which are useful as antihypertensive agents.

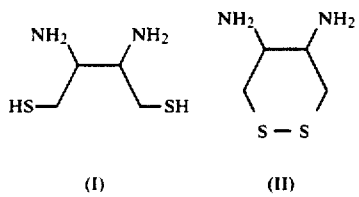

The N-acyl and N-alkyl derivatives of compounds (I) and (II) have the following structures:

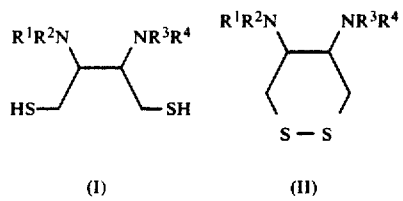

wherein $R^1$, $R^2$, $R^3$, and $R^4$ (collectively, for convenience, R) are independently selected from: H, substituted and unsubstituted acyl

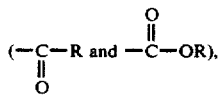

alkyl having 1-6 carbon atoms, aryl, arylalkyl, heteroaryl, and heteroarylalkyl; wherein, for example, the aryl is phenyl or thienyl; the alkyl moieties have from 1-4 carbon atoms; and substituent or substituents are selected from halogen (Cl, Br, F), alkyl having from 1-6 carbon atoms, amino, carboxyl, and hydroxyl. (Compounds I and II and the above-described derivatives thereof are collectively, for convenience, referred to throughout the remainder of this specification as "Compounds I and II".) Also included are the pharmaceutically acceptable salts of compounds I and II. The above-described compounds are also useful as radioprotective agents.

This invention also relates to processes for preparing compounds I and II; pharmaceutical compositions comprising compounds I and II; and methods of treatment comprising administering such compounds and compositions when an antihypertensive, or radioprotective, effect is indicated.

DETAILED DESCRIPTION OF THE INVENTION

Both the DL and meso configurations of compounds I and II are preferred. They are conveniently prepared by the following scheme.

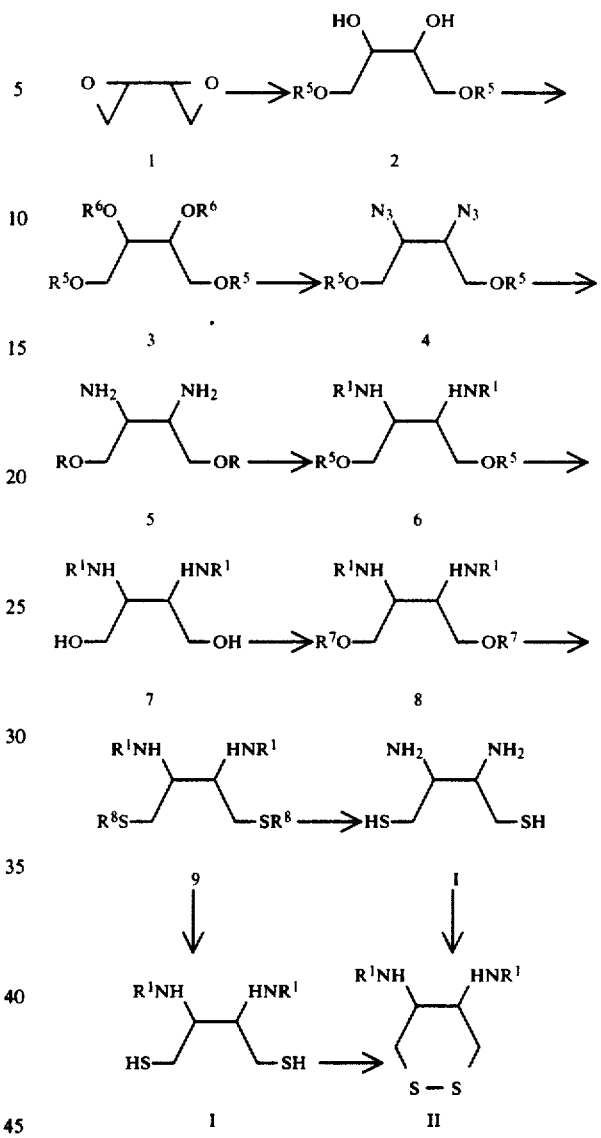

In words relative to the above scheme, it should be noted that the DL and S,S forms of 8 ($R^1$=ethyloxycarbonyl; $R^7$=methanesulfonate) and their synthesis from the corresponding butadiene diepoxide are known. In the general scheme of the present invention, the transformation of DL-butadiene diepoxide (1) to DL-8 is accomplished by treating 1 with a strong base, such as, a sodium alhoxide or aryloxide, for example, $C_6H_5CH_2ONa$, or the like, in the presence of the alcohol $R^5OH$ ($R^5$=alkyl, arylkyl) at a temperature of from 25° to 100° C. for from 4 to 48 hours. Meso-2 is conveniently prepared by treating the suitably protected trans-2-butene-1,4-diol with an oxidant, such as hydrogen peroxide, in formic acid at 40° to 60° C. for 1 to 6 hours followed by exposure to aqueous base, such as sodium hydrioxide, at 30° to 50° C. for 0.5 to 2 hours. In addition, D or L-2 are prepared from diethyl D orL-tartrate in a sequence of four steps involving: acetonide formation utilizing the 2,3-diol functionality, lithuim aluminum hydride reduction of the esters to the 1,4-diol, benzl ether formation, and acetonide hydrolysis.

The following transformations involving C-2 and C-3 are stereospecific.

The transformation 2 to 3 is accomplished by treating 2 with an alkyl- or arylkylsulfonyl halide, such as methanesulfonyl chloride, benzenesulfonyl chloride, toluenesulfonyl chloride, or the like in a solvent, such as diethyl ether, THF, methylene chloride with triethylamine, pyridine or DMAP, or the like, at a temperature of from 0° to 50° C. for from 1 to 24 hours.

Diazide 4 is obtained from 3 on heating with sodium azide in a solvent such as dimethylformamide (DMF), dimethyl sulfoxide, N-methyl pyrrolidinone, or the like, at a temperature of from 25° to 150° C. for from 4 to 48 hours.

The reduction 4 to 5 is accomplished by treating 4 with a reducing agent such as lithium aluminum hydride, or the like, in a solvent such as diethyl ether tetrahydrofuran, dioxane, or the like, at a temperature of from 0° to 100° C. for from 1 to 4 hours.

The N-acylation 5 to 6 is accomplished by treating 5 with the acylating agent of choice, and in a sequence and reaction ratio to achieve N-substituent patterns with $R^1$, $R^2$, $R^3$, and $R^4$, above defined, of choice according to acylation procedures well known in the art. Representative acylating agents include: ethyl chloroformate, methyl chloroformate, acetic anhydride, acetic-formic anhydride, pivaoyl chloride, BOC-ON ([2-(t-butoxycarbonyloxyimino)-2-phenylacetonitrile]), or the like.

The reaction 6 to 7 is typically accomplished by hydrogenation in the presence of a catalysis such as platinum or palladium or carbon in a solvent such ethanol under a pressure of 1 to 4 atmospheres of $H_2$ at a temperature of from 25° to 50° C. for from 1 to 6 hours.

The transformation 7 to 8 is accomplished by treating 7 with an alkyl- or arylsulfonyl halide, such as methanesulfonyl chloride, benzenesulfonyl chloride, toluenesulfonyl chloride, or the like, in a solvent, such as pyridine or ether, THF, or methylene chloride in the presence of pyridine, $Et_3N$ or DMAP, or the like, at a temperature of from 0° to 50° C. for from 1 to 12 hours. With respect to radical $R^6$ of 8, its precise identity depends on the sulfonating agent taken in reaction.

The transformation 8 to 9

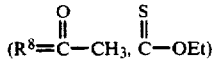

is typically accomplished by treating 8 with potassium thioacetate, potassium ethyl xanthate, or the like, in a solvent such as DMF, DMSO, N-methyl prrolidinone, ethanol, or the like, at a temperature of from 0° to 50° C. for from 1 to 12 hours.

The deblocking transformation 9 to I is typically achieved by acid hydrolysis with I being isolated as the N-acid addition salt. Mild hydrolysis conditions will convert 9 to the dithiol species leaving the N-acyl groups intact. Removal of N-acyl functions in addition to conversion to the dithiol form is accomplished under harsher conditions, for example, on refluxing in concentrated aqueous HCl for 6 to 12 hours.

Conversion of I to the dithiane II is accomplished by treating I in the presence of strong base in a solvent such as water, methanol, ethanol, isopropanol, or the like for from 1 to 12 hours at 0° to 25° C. Suitable bases include aqueous NaOH, NaOR, $Na_2CO_3$, or the like. A preferred scheme involves aqueous NaOH in the presence of air. (R=alkyl having 1-4 carbon atoms.)

N-alkyl derivatives of I are readily prepared from II by acylation using acetic anhydride or acetic-formic anhydride, or the like, in a solvent, such as pyridine or ether, THF, or methylene chloride in the presence of pyridine, $Et_3N$, or DMAP, or the like, at 0° to 50° C. for from 1 to 12 hours followed by lithium aluminum hydride reduction. Oxidation of the so derivatized I, as described above, then provides N-alkyl derivatives of II. Repetition of this sequence using a different acylating agent in step one allows the preparation of derivatized I and II carrying two different N-alkyl groups.

UTILITY STATEMENT

The compounds of the present invention are useful as antihypertensives. They may be administered orally, parenterally by injection or by rectal suppository. Oral administration by tablet or capsule is preferred; wherein the final dosage form is prepared according to well known practices to ensure timely dissolution and availability. Typically the dose is from 0.1 to 10 mg per Kg of body weight given 1 to 3 times per day. The exact dosage regimen will be at the routine discretion of clinician taking into account the medical and physical history of the subject.

The compounds of the present invention also demonstrate an effect against the damaging effects of high energy, ionizing radiation in mammalian tissue. For humans the effective dosage range is 1–20 mg/kg body weight.

The following examples illustrate, but do not limit the product, process, compositional or method of treatment aspects of the present invention.

EXAMPLE 1

The Synthesis of Threo-2,3-Diamino-1,4-Butanedithiol; Its Dithiane; Derivatives Thereof; and Intermediates In the overall scheme for Example 1, the following abbreviations have been used: Bzl for $CH_2C_6H_5$; Ms for $CH_3SO_2$; and Ac for $CH_3CO$.

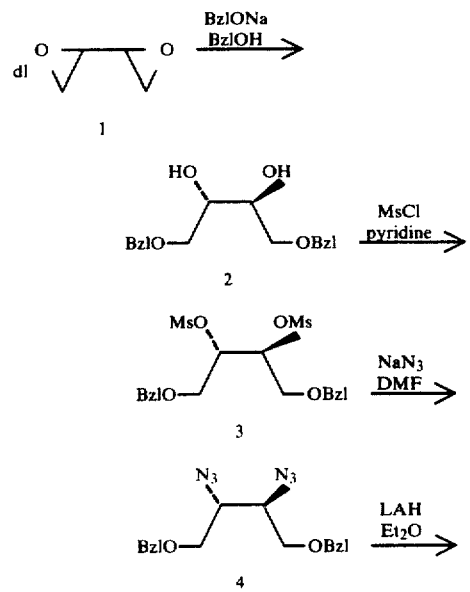

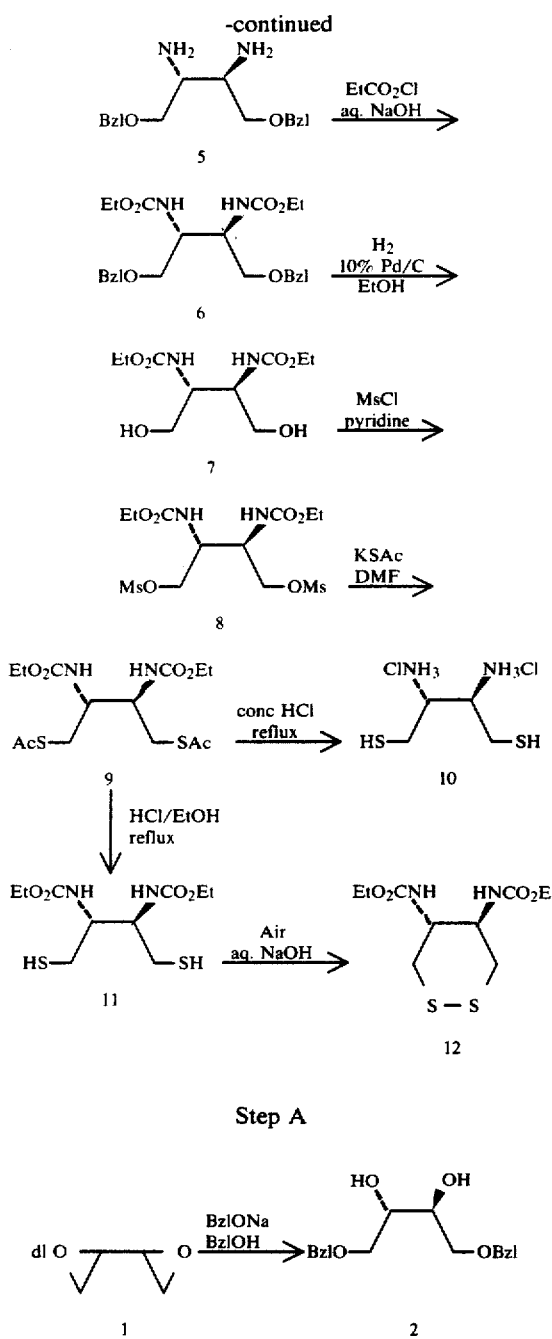

Step A

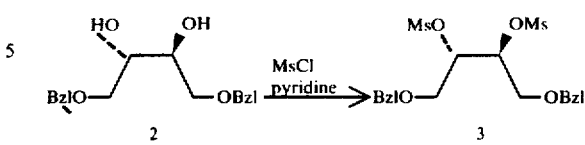

threo-1,4-Dibenzyloxy-2,3-butanediol (2)

dl-Butadiene diepoxide (1) (49.8 g, 0.578 mol) was aded dropwise over 30 minutes at 55°–85° C. to a stirred solution of sodium (15.5 g, 0.674 mol) in 348 g benzyl alcohol. After the reaction mixture had been stirred at room temperature for 20 hours, it was transferred to a separatory funnel with 500 mL diethyl ether and 1 L aqueous 1N sulfuric acid. The mixture was shaken well and the aqueous layer was removed. The ether extract was washed (1×500 mL water), dried (MgSO$_4$) and concentrated. Removal of the benzyl alcohol by high vacuum distillation left the diol 2, 165 g (94), which was used in the next step without further purification.

Step B

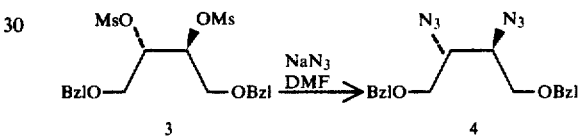

threo-1,4-Dibenzyloxy-2,3-butanediol 2,3-bismethanesulfonate (3)

Methanesulfonyl choride (185 g, 1.61 mol) was added dropwise over 2 hours and 20 minutes to a stirred, ice-cold solution of threo-1,4-dibenzyloxy-2,3-butanediol (2) (163 g, 0.539 mol) in 490 mL pyridine. After being stirred at room temperature for 20 hours, the reaction mixture was poured into 2.2. L of 3N aqueous hydrochloric acid. The majority of the aqueous phase was decanted from the oil that separated and was extracted (2×200 mL) with chloroform. The oil was dissolved in 250 mL chloroform, separated from what water was present, and combined with the other chloroform extracts. Drying (MgSO$_4$) and concentration left an oil which solidified on standing. Recrystallization from ethanol gave 3, 217 g (88%).

Step C

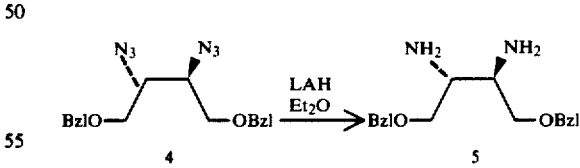

threo-2,3-Diazido-1,4-dibenzyloxybutane (4)

Sodium azide (49.6 g, 0.763 mol) was added to a solution of threo-1,4-dibenzyloxy-2,3-butanediol 2,3-bismethanesulfonate (3) (100 g, 0.218 mol) in 500 mL dimethylformamide. The mixture was heated to 100° C. and maintained at that temperature for 8 hours. After cooling to room temperature, the mixture was filtered and the majority of the dimethylformamide was removed under pressure. The residue was extracted with 500 mL diethyl ether. Filtration through celite and concentration left crude 4, 79.1 g (103%), which was used in the next step without further purification.

Step D threo-2,3-Diamino-1,4-dibenzyloxybutane (5)

A solution of crude threo-2,3-diazido-1,4-dibenzyloxybutane (4) (79.1 g, max. theory 0.218 mol) in 200 mL dry diethyl ether was added dropwise over 3 hours to a stirred suspension of lithium aluminum hydride (16.5 g, 0.435 mol) in 1500 mL dry diethyl ether. After refluxing an additional hour, the mixture was cooled in ice and the excess lithium aluminum hydride was destroyed by cautiously adding water. The ether filtrate obtained after filtration through celite was dried (MgSO$_4$) and concentrated to leave 5, 59.8 g (91% from 3). The material was used in the next step without further purification.

Step E

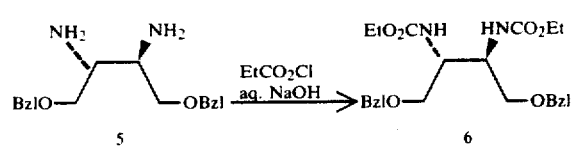

threo-N,N'-Dicarbethoxy-2,3-diamino-1,4-dibenzyloxybutane (6)

Ethyl chloroformate (34.0 g, 0.314 mol) was added dropwise over 25 minutes to a stirred, ice-cold mixture of threo-2,3-diamino-1,4-dibenzyloxybutane (5) (30.0 g, 0.100 mol), 21 g sodium hydroxide, and 300 mL water. After 3 hours on ice, 30 mL of concentrated hydrochloric acid was added slowly and the mixture was extracted (3×200 mL) with diethyl ether. Drying (MgSO$_4$) and concentration left 6, 44.0 g (99%), which was used in the next step without further purification.

Step F

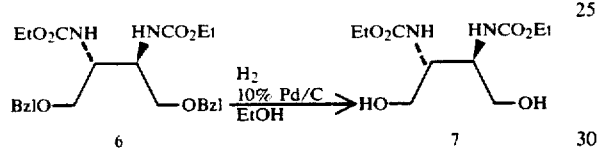

threo-N,N'-Dicarbethoxy-2,3-diamino-1,4-butanediol (7)

A mixture of threo-N,N'-dicarbethoxy-2,3-diamino-1,4-dibenzyloxybutane (6) (44.0 g, 0.100 mol), 400 mL absolute ethanol, 20 mL concentrated hydrochloric acid, and 2.0 g 10% palladium on carbon was placed in a 1 L bomb and stirred under 40 psi hydrogen for 2.5 hours. After removal of the cataylst by filtration through celite, the filtrate was concentrated and the residue was twice taken up in 200 mL chloroform and concentrated to remove trace ethanol. Crude 7, 26.9 g (100%), was left as a pale yellow oil and was used in the next step without further purification.

Step G

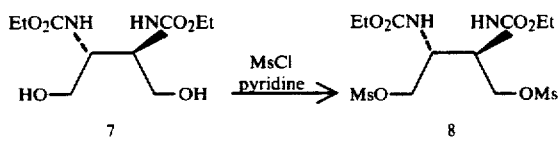

threo-N,N'-Dicarbethoxy-2,3-diamino-1,4-butanediol 1,4-bismethanesulfonate (8)

Methanesulfonyl chloride (34.4 g, 0.300 mol) was added dropwise over 45 minutes to a stirred, ice-cold solution of threo-N,N'-dicarbethoxy-2,3-diamino-1,4-butanediol (7) (26.4 g, 0.100 mol) in 130 mL pyridine. After having stirred in ice for 1 hour, 200 mL chloroform was added followed by 410 mL 4N aqueous hydrochloric acid. The mixture was transferred to a separatory funnel, the organic phase was separated, and the aqueous portion was extracted (2×100 mL) with chloroform. The combined organic extracts were washed (2×50 mL) with 1N aqueous hydrochloric acid and (1×100 mL) brine, dried (MgSO$_4$), and concentrated to leave 38 g crude 8. After triturating with 100 mL absolute ethanol and filtrating, the filter cake was washed with diethyl ether and dried in vacuo to leave 8, 26.1 g (62%), of sufficient purity to be used in the next step.

Step H

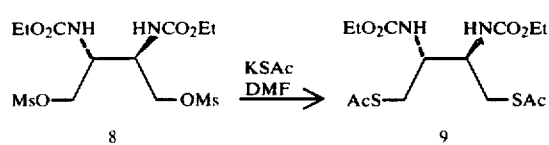

threo-1,2-Dimethylmercaptoethylene dicarbamic acid diethyl ester diacetate (9)

A mixture of threo-N,N'-dicarbethoxy-2,3-diamino-1,4-butanediol 4,4-bismethanesulfonate (8) (2.28 g, 5.43 mmol) and potassium thioacetate (1.55 g, 13.6 mmol) in 85 mL of dimethyl-formamide was stirred at room temperature for 15 hours. The majority of the dimethyl-formamide was removed under reduced pressure and the residue was taken up in 50 mL of wafter and extracted (3×40 mL) with chloroform. The combined extracts were dried (MgSO$_4$) and concentrated to leave a residue which was chromatographed (Waters Prep 500A, one silica cartridge, 30% ethyl acetate/hexane) to provide pure 9, 1.45 g (70%); m.p. 94°-97° C.

Step I

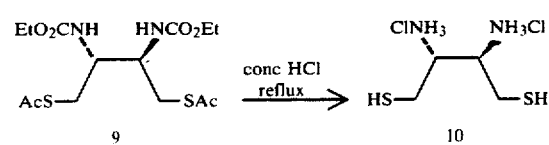

threo-2,3-Diamino-1,4-butanedithiol dihydrochloride (10)

A solution of threo-1,2-dimethylmercaptoethylene dicarbamic acid diethyl ester diacetate (9) (1.67 g, 4.39 mmol) in 150 mL of concentrated hydrochloric acid was refluxed under nitrogen for 18 hours. The reaction mixture was evaporated to dryness under reduced pressure and trace water was removed azeotropically with benzene. The residue was recrystallized from methanol/benzene with charcoal treatment to provide 10, 400 mg (41%). A second crop of less pure material weighing 330 mg was obtained by concentrating the filtrate.

Step J

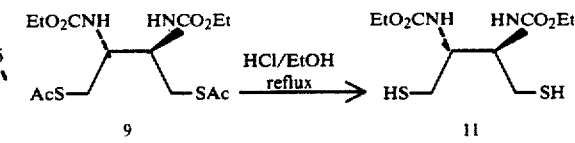

threo-1,2-Dimethylmercaptoethylene dicarbamic acid diethyl ester (11)

A solution of threo-1,2-dimethylmercaptoethylene dicarbamic acid diethyl ester diacetate (9) (1.06 g, 2.79 mmol) in 75 mL of saturated ethanolic hydrogen chloride was refluxed under nitrogen for 12 hours. The mixture was evaporated to dryness and trace ethanol was removed azeotropically with benzene. The residue was flash chromatographed (20 mm×6 in bed of 0.040–0.063 mm silica gel, 1% methanol/chloroform) to provide pure 11, 540 mg (65%); m.p. 107°–109° C.

Step K

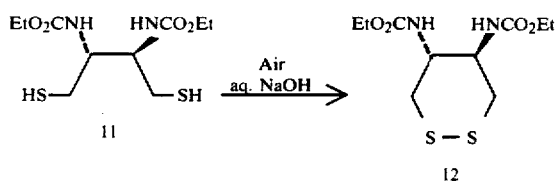

trans-4,5-di(N-carbonylethoxyamino)-1,2-dithiane (12)

Air was bubbled through a stirred solution of threo-1,2-dimethylmercaptoethylene dicarbamic acid diethyl ester (11) (1.54 g, 5.23 mmol) in 9 mL of 2N aqueous sodium hydroxide for 18 hours. The mixture was diluted 400 mL of cold water and precipitate was collected by filtration to provide 980 mg of crude product. Recrystallization from ethyl acetate/hexane gave pure 12, 650 mg (42%); m.p. 180°–182° C.

EXAMPLE 2

Following the foregoing Example 1 and text, the compounds of Example 2, Table 1, are prepared by analogy. Departures from established procedure are indicated under the heading "Remarks":

TABLE 1

| No. | Compound | | Remarks |
|---|---|---|---|
| III | $\begin{array}{c}NH_2 \quad NH_2 \\ HS \diagup \diagdown SH\end{array}$ | (meso) 2HCl | Prepared from meso-2 obtained by the trans hydroxylation of trans-1,4-dibenzyloxy-2-butene. |
| IV | $\begin{array}{c}NH_2 \quad NH_2 \\ HS \diagup \diagdown SH\end{array}$ | (D) 2HCl | Prepared from D-2 derived from D-diethyl tartrate as described in text. |
| V | $\begin{array}{c}NH_2 \quad NH_2 \\ HS \diagup \diagdown SH\end{array}$ | (L) 2HCl | Prepared from L-2 derived from L-diethyl tartrate as described in text. |
| VI | $\begin{array}{c}AcNH \quad HNAc \\ HS \diagup \diagdown SH\end{array}$ | (DL) | Obtained by the substitution of acetic anhydride in Step E. |
| VII | $\begin{array}{c}CH_3NH \quad HNCH_3 \\ HS \diagup \diagdown SH\end{array}$ | (DL) 2HCl | Obtained by the formulation of II ($R^1$ = H) with acetic-formic anhydride followed by lithium aluminum hydride reduction. |
| VIII | $\begin{array}{c}Et \quad Et \\ CH_3N \quad NCH_3 \\ HS \diagup \diagdown SH\end{array}$ | (DL) 2HCl | Obtained by the acetylation of the oxidized form of VII with acetic anhydride followed by lithium aluminum hydride reduction. |

It is understood that the meso, D, and L isomers of compounds VI–VIII are prepared by analogy.

EXAMPLE 3

A dry solid pharmaceutical composition is prepared by mixing the following materials together in the proportions by weight specified:

2,3-Diamino-1,4-Butanedithiol: 50
Sodium Citrate: 20
Alginic Acid: 5
Polyvinylpyrrolidone: 15
Magnesium Stearate: 5

The dry composition is thoroughly blended, and tablets are punched from the resulting mixture, each tablet being of such size that it contains 100 mg of the active ingredient. Other tablets are also prepared in a manner containing 10, 25, and 200 mg of active ingredient, respectively, by using an appropriate quantity by weight of the active in each case.

EXAMPLE 4

A dry solid pharmaceutical composition is prepared by combining the following materials together in the weight proportions indicated below:

N,N-dimethyl-2,3-Diamino-1,4-Butanedithiol: 50
Calcium Carbonate: 20
Polyethylene glycol:
(Average Molecular Weight 600): 30

The dried solid mixture is thoroughly mixed until uniform in composition. The powdered product is then used to fill soft elastic and hard-gelatin capsules so as to provide capsules containing 200 mg of the active ingredient.

What is claimed is:

1. A method of treating hypertension comprising administering an anti-hypertensive effective amount of a composition which comprises as the active ingredient, a compound selected from the group consisting of:

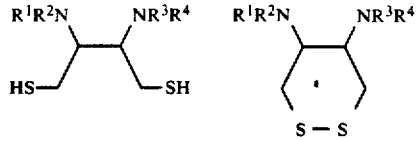

wherein: $R^1$, $R^2$, $R^3$, and $R^4$ are independently selected from the group consisting of: H,

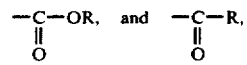

and wherein R, $R^1$, $R^2$, $R^3$, and $R^4$ are selected from the group consisting of substituted and unsubstituted alkyl having 1–6 carbon atoms and phenyl, wherein said alkyl moieties have from 1–4 carbon atoms; and wherein said substituent or substituents are selected from the group consisting of halogen, alkyl having from 1–6 carbon atoms, amino, carboxyl, and hydroxyl; and the pharmaceutically acceptable salts thereof.

2. A method according to claim 1 wherein $R^1$ and $R^3$ are hydrogen and $R^2$ and $R^4$ are

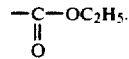

3. A method according to claim 1 wherein $R^1$ and $R^3$ are ethyl and $R^2$ and $R^4$ are methyl.

4. A method according to claim 1 wherein $R^1$, $R^2$, $R^3$ and $R^4$ are hydrogen.

5. A method according to claim 1 wherein $R^1$ and $R^3$ are hydrogen and $R^2$ and $R^4$ are methyl.

6. A method according to claim 1 wherein $R^3$ and $R^4$ are selected from the group consisting of alkyl of 1 to 6 carbon atoms,

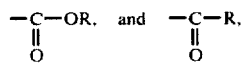

where R is alkyl of 1 to 6 carbon atoms.

7. A method according to claim 1 wherein the composition contains a pharmaceutically acceptable carrier.

* * * * *

UNITED STATES PATENT AND TRADEMARK OFFICE
CERTIFICATE OF CORRECTION

PATENT NO. : 4,659,733

DATED : April 21, 1987

INVENTOR(S) : Mark T. DuPriest, Billie M. York, Jr.

It is certified that error appears in the above-identified patent and that said Letters Patent is hereby corrected as shown below:

Column 1, line 8, change "2,3 diamino", to --2,3-diamino--.

Column 2, line 54, change "alhoxide" to --alkoxide--.

Column 2, line 56, change "arylkvl" to --arylakyl--.

Column 2, line 62, change "hydrioxide" to --hydroxide--.

Column 2, line 63, insert space between "orL-tar" to read --or L-tar--.

Column 2, line 67, change "benzl" to --benzyl--.

Column 3, line 4, change "arylkylsulfonyl" to --arylakylsulfonyl--.

Column 3, line 31, change "catalysis" to --catalyst--.

Column 3, line 42, change "$R^6$" to --$R^7$--.

Column 3, line 52, change "prrolidinone" to --pyrrolidinone--.

Column 5, line 56, change "aded" to --added--.

Column 5, line 57, after "348 g" insert --of--.

Column 5, line 65, change "(94)" to --(94%)--.

Column 6, line 17, change "2.2." to --2.2--.

Column 7, line 39, change "cataylst" to --catalyst--.

Column 8, line 17, change "4,4" to --1,4--.

UNITED STATES PATENT AND TRADEMARK OFFICE
CERTIFICATE OF CORRECTION

PATENT NO. : 4,659,733

DATED : April 21, 1987

INVENTOR(S) : Mark T. DuPriest, Billie M. York, Jr.

It is certified that error appears in the above-identified patent and that said Letters Patent is hereby corrected as shown below:

Column 8, line 19, change -dimethyl-formamide" to --dimethylformamide--.

Column 8, line 22, change "wafter" to --water--.

Column 9, line 20, after "luted" insert --with--; and after "and" insert --the--.

Signed and Sealed this

Twenty-first Day of June, 1988

Attest:

DONALD J. QUIGG

Attesting Officer

Commissioner of Patents and Trademarks